United States Patent [19]

Bennett

[11] Patent Number: Plant 6,138

[45] Date of Patent: Mar. 29, 1988

[54] MINIATURE ROSE PLANT NAMED 'LITTLE PEACHES'

[76] Inventor: Cecilia L. D. Bennett, 489 Minot Ave., Chula Vista, Calif. 92010

[21] Appl. No.: 825,758

[22] Filed: Feb. 3, 1986

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant, named 'Little Peaches', which is characterized by its soft yellow blooms, ranging from Primrose Yellow to Mimosa Yellow with the outer margins blushing Empire Rose to Delft Rose, usually one to a stem with hybrid tea form. The bush is compact, well-branched and produces moderate to heavy quantities of bloom.

1 Drawing Figure

The present invention relates to a new and distinct variety of a hardy, dwarf, bush plant of the miniature class; the variety being primarily characterized as a yellow blend.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 10 to 15 inches (30 to 40 cm). The canes are sturdy and erect with moderate branching and medium to heavy foliage covering. The plant is a moderate to heavy bloomer that does well either in the green house or outdoors.

The plant has good growth habits well-shaped and attractive, bearing numerous leaflets of average size.

The seed parent was Electron (U.S. Plant Pat. No. 3,226), and the pollen parent was Fairest of Fair (U.S. Plant Pat. No. 5,260). It differs from its seed parent in the following ways. It is a miniature of the yellow blend classification rather than a hybrid tea of the deep pink classification. It differs from its pollen parent in the following ways. It is a yellow blend with marked blushing over the surface of all petals as the bloom matures. Fairest of Fair is light yellow with no other colors present.

The descriptive matter which follows, pertains to roses grown and color values observed in plants and newly opened blooms in the months of March through August 1984. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Little Peaches', the following is a detailed description thereof in outline; all major color plate identifications being by reference to the British Colour Council Horticultural Colour Chart, except where common terms of color definition are employed.

Type: Hardy, dwarf, bushy, green house or outdoor, exhibition quality or garden decorative potted plant.

Class: Miniature.

Variety name: Little Peaches.

Flower borne: Usually one to a stem, but occasionally in sprays of 3 to 5 or more on erect stems with foliage well below the blooms.

Quantity of bloom: Moderate to heavy both outdoors or green house grown.

Bud:

*Peduncle.*—Average length (15 to 25 mm); average diameter and sturdy; ranging from near Lettuce Green (861/1 to 861/3 page 176) to near Scheeles Green (860/1 to 860/3 page 175) with occasional tinting of bronze.

*Hairs.*—Extremely small and numerous with a reddish color; located over the entire surface of the peduncle and sepals, but not present on the calyx tube.

*Calyx.*—Color ranging from near Lettuce Green (861/1 to 861/3 page 176) to near Scheeles Green (860/1 to 860/3 page 175). Opening — Opens well in all weather.

Bloom: Size when fully open — Average for a miniature variety (40 to 45 mm).

*Petalage.*—Full — averaging about 30 to 35 petals, arranged regularly, plus petaloids (5 to 15 or more).

*Form.*—Urn-shaped to ovoid as the bloom progresses. The petals remain at first somewhat tightly cupped with the tips and/or margins reflexed outward, becoming at maturity more loosely cupped; and the petals reflex more tightly (quilling), until each row of petals forms a five pointed star.

Petals: Fairly thick with good substance; both the upper and under surfaces of all petals have a matte finish.

*Shape.*—Outer petals are of a very broad obovate form with a slight peak at the apex. The intermediate petals are very much like the outer petals only narrower. The inner petals are a broad lanceolate form; and the petaloids are also lanceolate form with some occasional irregularities.

Color: Newly opened flowers from plants grown outdoors (March 1984 through August 1984), Chula Vista, Calif.

*Outside petals.*—Upper surface — Outer Margin — having a blush ranging from near Empire Rose (0621 to 0621/2 page 183) to near Delft Rose (020/1 to 020/3 page 108). Body of petal — Ranging from near Primrose Yellow (601/1 to 601/3 page 65) to near Mimosa Yellow (602/1 to 602/3 page 143) with a base ranging from near Primrose Yellow (601/1 to 601/2 page 65) to near Mimosa Yellow (602/1 to 602/2 page 143). Under surface — Ranging from near Primrose Yellow (601/2 to 601/3 page 65) to near Mimosa Yellow (602/1 to 602/3 page 143) with an occasional blush of near Empire Rose (0621 to 0621/2 page 183) to near Delft Rose (021/1 to 021/3 page 109).

*Intermediate petals.*—Upper surface — Ranging from near Primrose Yellow (601/1 to 601/3 page 65) to near Mimosa Yellow (602/1 to 602/3 page 43) with an occasional blush of near Empire Rose (0621/1 to 0621/3 page 183). Under surface — Ranging from near Primrose Yellow (601/1 to 601/2 page 65) to near Mimosa Yellow (602/1 to 602/2 page 143).

*Inner petals.*—Upper surface — Ranging from near Primrose Yellow (601/1 to 601/3 page 65) to near Mimosa Yellow (602/1 to 602/3 page 43) with an occasional touch of near Empire Rose (0621/3 page 183) at the outermost edge and/or tip of petal. Under surface — Ranging from near Primrose Yellow (601/1 to 601/2 page 65) to near Mimosa Yellow (602/1 to 602/3 page 43).

*General color effect.*—Newly opened flowers — Pale yellow blooms with soft blushing of margins on the outermost petals. Three days open — Some fading of yellow on the outer petals with deepening and spreading of the blush tones into the body of the petals, and some blushing present on the intermediate petal margins. Five to seven days — Increased fading of yellow with touches of blush on tips and edges of inner petals and extreme blushing of outermost petals. Quilling effect present on all petals. After seven days — Petals fading to near white with deep blush overlaying all sun-exposed surfaces.

*Flower longevity.*—(March to August 1984) Plant in pot 4 to 7 days from bud with sepals reflexed to fully opened bloom. Holding at fully opened with gradual fading of yellow tones and increased deepening of blush tones for 5 to 7 days or longer. Cut blooms at living room temperature 3 to 5 days or longer.

Reproductive organs:

*Stamens.*—A generous amount arranged uniformly around the pistil.

*Filaments.*—Varying in length with shorter filaments more proximal to the pistil; bright yellow color, including the anthers.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seed.*—Few or none.

*Sepals.*—Permanent; spear-shaped; open as the bloom opens, but does not recurve against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Ranging from very dark Garnet Brown (page 192) on new foliage through near Fern Green (0862 to 0862/1 page 186) to near Spinach Green (0960 to 0960/3 page 187) as the foliage matures, with occasional bronzing of the margins, especially noticeable on the newer foliage. The upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length form small to medium; average width; tapering auricles angled outward at about 45 degrees.

Growth:

*Habit.*—Dwarf, bushy; small to average height for a miniature rose plant.

*Growth.*—Compact and well-branched.

*Canes.*—Medium diameter; sturdy; held erect.

*Main stems.*—Color — Ranging from near Scheeles Green (860 to 860/2 page 175) to near Spinach Green (0960 to 0960/3 page 187).

*Thorns.*—Averaging 5 to 10 per 10 cm on the main stems and fewer on the branches. Pale yellow color with occasional tinting of bronze. Small to average in size. Slender and hooked slightly downward.

*Branches.*—Color — Same as main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant named 'Little Peaches' of hardy, dwarf, compact growth, well-branched and attractive appearance, substantially as illustrated and described, characterized by its blooms of soft yellow, ranging from Primrose Yellow to Mimosa Yellow with the outer margins blushing Empire Rose to Delft Rose, easily asexually reproduced from cuttings, with flowers borne usually one to a stem, but occasionally in sprays of 3 to 5 or more.

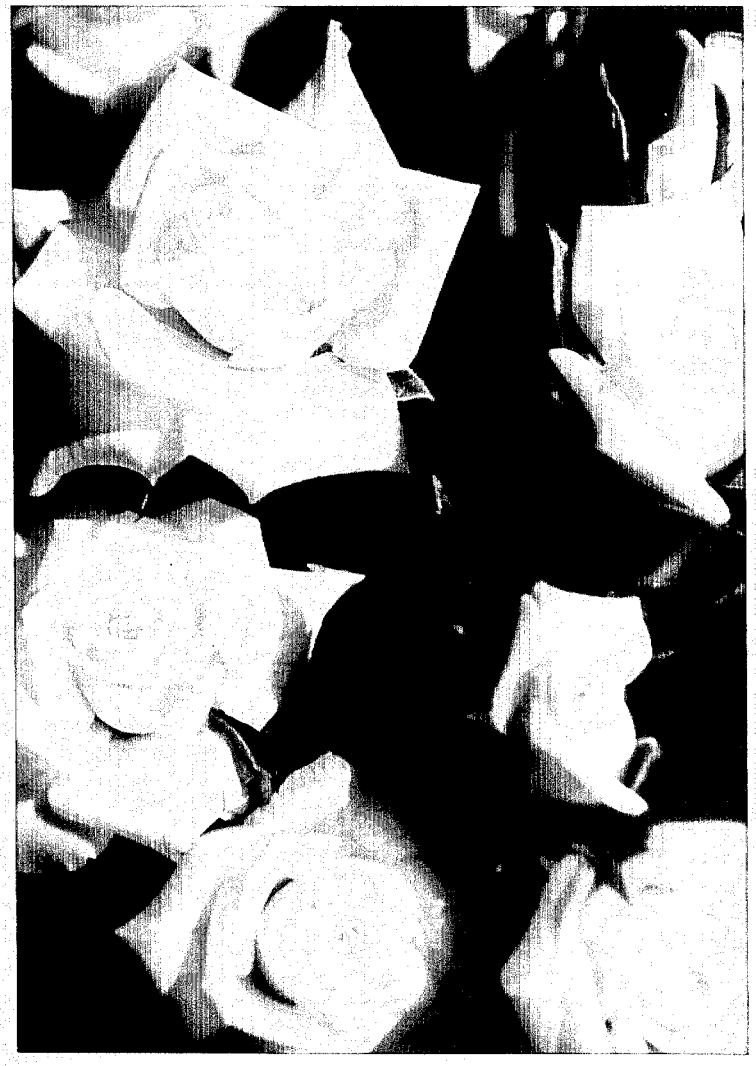

* * * * *